United States Patent [19]
Schmidt et al.

[11] Patent Number: 5,371,203
[45] Date of Patent: Dec. 6, 1994

[54] PROCESS FOR THE STEREOSELECTIVE PREPARATION OF β-FUCOPYRANOSYL PHOSPHATES AND VERY PURE GDP-FUCOSE

[75] Inventors: Richard R. Schmidt; Karl-Heinz Jung, both of Konstanz; Barbara Spahngehl, Munich; Willy Kinzy, Inzlingen; Jürgen Hemberger, Aschaffenburg, all of Germany

[73] Assignee: Merck Patent Gesellschaft Mit Beschrankter Haftung, Darmstadt, Germany

[21] Appl. No.: 828,617

[22] Filed: Jan. 31, 1992

[30] Foreign Application Priority Data

Jan. 31, 1991 [DE] Germany ............................ 4102817

[51] Int. Cl.$^5$ .................. C07H 11/04; C07H 1/00
[52] U.S. Cl. ............................. 536/17.9; 536/18.7; 536/55.3; 536/115; 536/117; 536/124
[58] Field of Search ............ 536/117, 17.2, 17.9, 536/18.7, 115, 116, 55.3, 124

[56] References Cited

U.S. PATENT DOCUMENTS 4,952,683  8/1990  Tschannen et al. ............... 536/17.9
4,987,271  1/1991  Watabe et al. ...................... 536/120

OTHER PUBLICATIONS

Chemical Abstracts, vol. 96, No. 23, issued 7 Jun. 1982, Asahi Chemical Industry Co., Ltd. "Production of Guanosine Diphosphate Fucose with Microorganisms," See page 522, Col. 2, abstract No. 197918s, 30 Jan. 1982, Appl. 80/92, 782, 09 Jul. 1980; 4 pages.

Chemical Abstracts, vol. 100, No. 21, issued 21 May 1984, Yamamoto et al, "Preparation of GDP-L-fucose by using microbial enzymes," See page 497 Col. 1, abstract No. 173093u, Biol. Chem. 1984, 4813h 823–4 (Eng).

Chemical Abstracts, vol. 113, No. 23, issued 3 Dec. 1990, Gokhale et al, "Chemical Synthesis of GDP-fucose analogs and their utilization by the Lewis α(1–34) Fucosyltransferase." See page 828, col. 2, abstract No. 212565q, Can. J. Chem. 1990, 68(7), 1063–71 (Eng).

Chemical Abstracts, vol. 115, No. 3, issued 22 Jul. 1991, Tochikura et al, "Guanosine Diphosphate L–Fucose and its Manufacture with Klebsiella Pneumoniae," see page 635, col. 1, abstract No. 27718v, 02 Nov. 1990, Appl. 89/89, 565, 07 Apr. 1989; 4 pages.

Chemical Abstracts, vol. 78, No. 17, issued 30 Apr. 1973, Prihar et al, "Chemical Synthesis of β-L-Furopyranosyl Phosphate and β-L-Rhamnopyranosyl Phosphate" see page 522, col. 1, abstract No. 111693h, Biochemistry 1973, 12(5), 997–1002 (Eng).

Chemical Abstracts, vol. 84, No. 13, issued 29. Mar. 1976, Prohaska et al, "simple and efficient method for the preparation of GDP–fucose." see page 240, col. 2, abstract No. 86417k, Anal. Biochem. 1975, 69(2), 536–44 (Eng).

Chemical Abstracts, vol. 88, No. 17, issued 24 Apr. 1978, Prihar et al, "Synthesis of β-L-fucopyranosyl Phosphate and L-Fucofuranosyl phosphates by the MacDonald Procedure." See page 581, col. 2, abstract No. 121561j, Carbohydr. Res. 1977, 56(2), 315–24 (Eng).

Chemical Abstracts, vol. 95, No. 19, issued 9 Nov. 1981, Nunez, et al, "the Synthesis and Characterization of α-and β-L-Fucopyranosyl Phosphates and GDP-Fucose." See page 794, col. 2, abstract No. 169680u, Can. J. Chem. 1981, 59(14), 2086–95 (Eng).

H. Nunez et al., "The synthesis and characterization of α-and β-L-fucopyranosyl ... ", Can. J. Chem. Vol. 59, pp. 2086–2095 (9181).

Primary Examiner—John W. Rollins
Assistant Examiner—Everett White
Attorney, Agent, or Firm—Millen, White, Zelano & Branigan

[57] ABSTRACT

The invention relates to a process for the stereoselective preparation of β-L-fucopyranosyl phosphates via the trichloroacetimidates of protected L-fucose and the synthesis and purification of very pure GDP-fucose from the β-L-fucopyranosyl phosphates.

17 Claims, 2 Drawing Sheets

PROCESS FOR THE STEREOSELECTIVE PREPARATION OF β-FUCOPYRANOSYL PHOSPHATES AND VERY PURE GDP-FUCOSE

SUMMARY OF THE INVENTION

The invention relates to a process for the stereoselective preparation of β-fucopyranosyl phosphates and of very pure guanosine diphosphate-fucose (GDP-fucose), which can be prepared from the former.

L-Fucose is known as a constituent of oligosaccharides of milk and of blood group substances (for example: Hakomori, Progr. Biochem. Pharmacol. 10 (1975), 167). The deoxyhexose is further involved in the synthesis of lipopolysaccharides of bacteria and glycosphingolipids of mammals (for example: Flowers, Adv. Carbohydr. Chem. 39 (1981), 279). Fucosylated glycolipids play an important role in the regulation of cell growth and cell differentiation. It is of particular interest, however, that fucosylated glycolipids are constituents of surface structures of tumor cells and display antigenic properties (for example: Hakomori, Ann. Rev. Biochem. 50 (1981), 733). They thus attain importance for tumor therapy and tumor diagnosis. The biosynthesis of fucose-containing oligosaccharides and glycolipids requires, inter alia, specific enzymes, the fucosyltransferases. The substrate for these fucosyltransferases is guanosine diphosphate-fucose (GDP-fucose).

For the investigation and production for tumor-associated antigens based on fucosylated glycolipids, it is therefore necessary to have relatively large amounts of very pure GDP-fucose available. In spite of the need, which has existed for a relatively long time, only one chemical synthesis (Nunez et al., Can. J. Chem. 59 (1981), 2086) and several enzymatic syntheses (for example: Yamamoto et al., Agric. Biol. Chem. 48 (1984), 823) of GDP-fucose have become known. The enzymatic syntheses which proceed, for example, via fucose-1-phosphate or via GDP-mannose, however, have the disadvantage that they yield only low amounts of GDP-fucose.

The key compound in the chemical synthesis of GDP-fucose is without doubt fucose-1-phosphate, whose provision in adequate amount is the limiting quantity in the total synthesis. Fucose-1-phosphate occurs in two different configurations, to be precise in the form of α-fucopyranosyl phosphate, which can be prepared relatively simply by the chlorophosphoamidate method (for example: Westerduin et al., Tetrahedron Lett. 27 (1986), 1211), and in the form of β-fucopyranosyl phosphate. The phosphate having the β-configuration is solely suitable for the synthesis of GDP-fucose. The known chemical syntheses of β-fucopyranosyl phosphate (Nunez et al., loc. cit.; Tsai et al., Carbohydr. Res. 64 (1978), 297) are distinguished, however, by a low stereoselectivity and/or low yield and in some cases are additionally expensive and complicated, so that at best they are suitable for preparation on the laboratory scale. The difficulty in the previous preparation of β-fucopyranosyl phosphate is no doubt to be sought in its pronounced lability, in particular to acids.

The known processes for the preparation of GDP-fucose from β-fucopyranosyl phosphate (Nunez et al., loc. cit.) furthermore has the disadvantage that the purification of the final product is only carried out by means of an ion exchanger, so that possibly further purification but at least desalting of the products is necessary for many biochemical purposes. However, this is again associated with losses in yield.

It has also been found that the α-trichloroacetimidates needed for this can easily be prepared stereoselectively in high yields by reaction of L-fucose or its forms protected on positions 2, 3 and 4 with trichloroacetonitrile, preferably using sodium hydride as base.

Finally, it has been found that the provision of GDP-fucose by reaction of the β-fucopyranosyl phosphates prepared according to the invention with activated GMP in a further process step according to the invention proceeds particularly advantageously if the β-fucopyranosyl phosphates are converted into an easily soluble salt, in particular the tri-n-octylammonium salt, it being possible to achieve the high purity of the GDP-fucose formed, by purification by means of HPLC using a volatile eluent and it moreover being possible to simplify the process.

The invention thus relates to a process for the selective preparation of β-fucopyranosyl phosphates, characterised in that L-fucose protected in positions 2, 3 and 4 is converted into the corresponding O-(α-L-fucopyranosyl) trichloroacetimidate, this is reacted with an absolutely acid-free organic phosphate of the formula PO (OH)(OR)$_2$, i.e., the reaction is conducted in the absence of acid in which R is C$_1$–C$_4$-alkyl, benzyl or phenyl, the radical R of the phosphate group and the protective groups on the fucopyranosyl ring are removed and the free β-L-fucopyranosyl phosphate is isolated as the salt.

The invention further relates to a process for the stereoselective preparation of very pure GDP-fucose, characterized in that β-L-fucopyranosyl phosphate is converted into an easily soluble salt, this is reacted with activated GMP and the GDP-fucose formed is purified by means of preparative HPLC using a volatile buffer system as the eluant.

The invention in particular relates to a corresponding process, which is characterized in that the β-fucopyranosyl phosphate employed is prepared by one of the processes described.

The process according to the invention is also distinguished in that the provision of, in particular, tri-O-acetyl-L-fucose from the tetra-acetylated compound can be carried out in a one-step reaction, preferably using hydrazine acetate, which contributes to the simplification of the total synthesis.

The invention thus also relates to a corresponding process, which is characterized in that 2,3,4-tri-O-acetyl-L-fucose is prepared from the tetra-acetylated L-fucose in a one-step reaction.

Upon further study of the specification and appended claims, further objects and advantages of this invention will become apparent to those skilled in the art.

If other types of bases are used in the reaction of 2,3,4-protected L-fucose with trichloroacetonitrile, different mixtures of α- and β-fucopyranosyl trichloroacetimidates are formed which first have to be separated for further use. When using sodium hydride analogous bases, the corresponding α-trichloroacetimidate is exclusively formed. The yields of α-imidates when using sodium hydride, relative, for example, to the tri-O-acetyl-L-fucose, are on average 70 to 80%.

The degree of purity, in particular the residual content of acids, of the phosphates of the type P(OH)(OR)$_2$ used in the reaction with the α-trichloroacetimidates of the protected L-fucose to give the fucopyranosyl phosphates determines the stereoselective course with respect to the anomers formed. The α-fucopyranosyl phosphates, which are not suitable for further processing to give GDP-fucose, form selectively if relatively small amounts of acids, such as, for example, boron trifluoride, are present in the phosphates used or are added to the reaction mixture. If, according to the invention, the β-fucopyranosyl phosphates are exclusively desired, the reaction must be carried out under strictly acid-free conditions. By "acid free" is generally meant an acid content of less than 1 wt. %, preferably less than 0.5 wt. %. The maximum upper limit of the acid content is about 1-2%. The yields of the β-anomers, relative to the corresponding α-trichloroacetimidate employed, are, according to the invention, between 85 and 95% after purification, preferably between 85 and 90%.

If the yields of β-fucopyranosyl phosphate of the synthesis according to the invention are compared, starting in the actual case from tri-O-acetyl-L-fucose via the imidate compound, with the yields of the two known chemical syntheses (Nunez et al., supra.; Tsai et al., supra.), the desired product is obtained (as the salt) by the process described with on average about a 70% yield, by the known process of Nunez et al. with about a 50% yield, and by the process of Tsai et al. (starting from the orthoacetate of L-fucose) with only about a 20% yield. In addition, the process according to the invention for the preparation of β-fucopyranosyl phosphates, in particular compared with the process of Nunez et al., has fewer and more simple process steps.

The total process according to the invention is distinguished by a high stereoselectivity, a low number of process steps, and simplicity. For example, no special separation of α- and β-anomers is necessary to obtain very good yields. Owing to the novel purification process, a very pure GDP-fucose, about 20-40% relative to dibenzyl or diphenyl 2,3,4-tri-O-acetyl-β-L-fucopyranosyl phosphate, which is also suitable for use in the most sensitive biochemical processes, can be obtained. The process is best suited to be employed on the relatively large industrial scale.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

Figure 1:
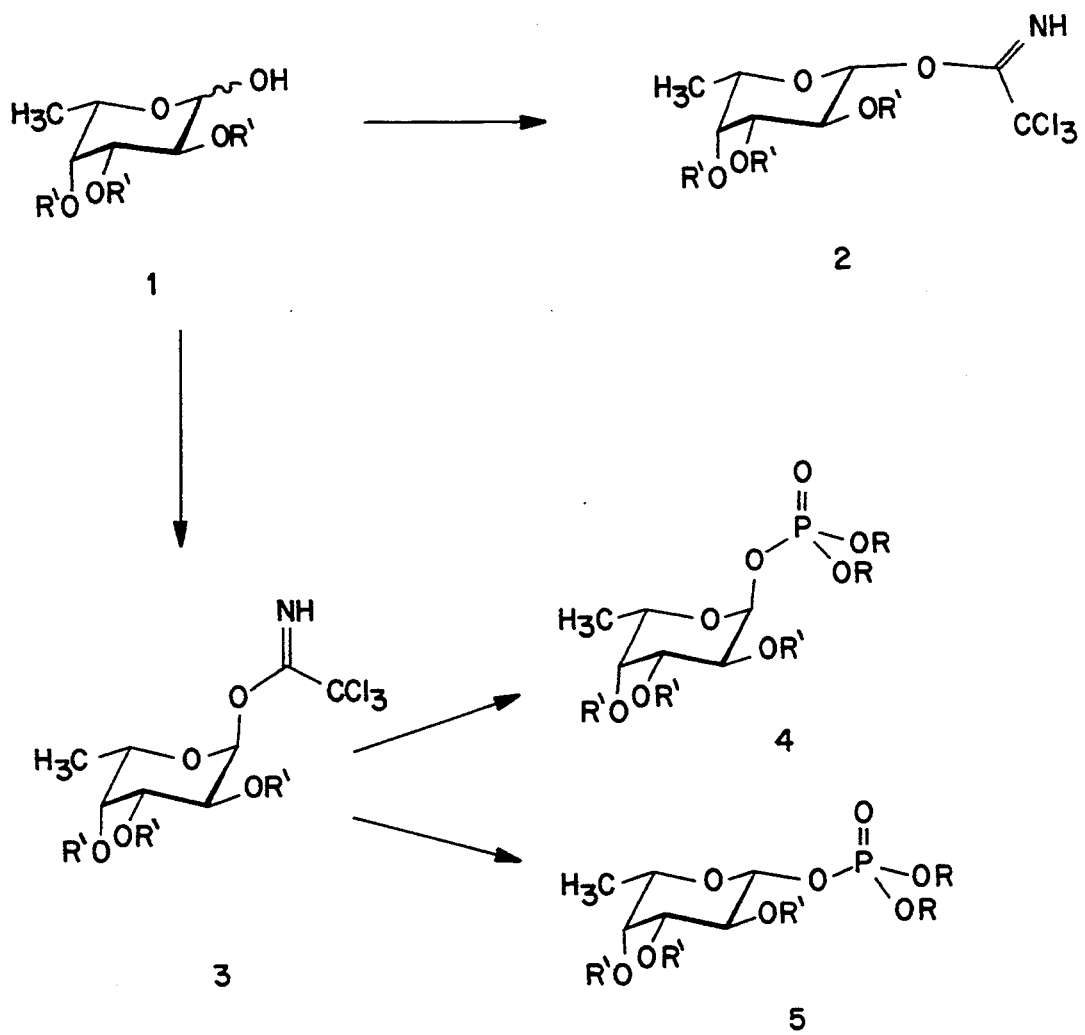
FIG. 1 is a synthesis scheme of the reaction of trisubstituted L-fucose to give the correspondingly protected α- and β-L-fucopyranosyl phosphates via the respective α-trichloroacetimidates. 1: trisubstituted L-fucose; 2: β-trichloroacetimidate of protected L-fucose; 3: α-trichloroacetimidate of L-fucose; 4: 2,3,4-protected α-L-fucopyranosyl phosphate; 5: 2,3, 4-protected β-L-fucopyranosyl phosphate; the symbols here in each case mean: $R'=R^1CO-$, $R^1$; $R^1$=alkyl ($C_1-C_4$), benzyl, phenyl; $R=R^1$.
Figure 2:
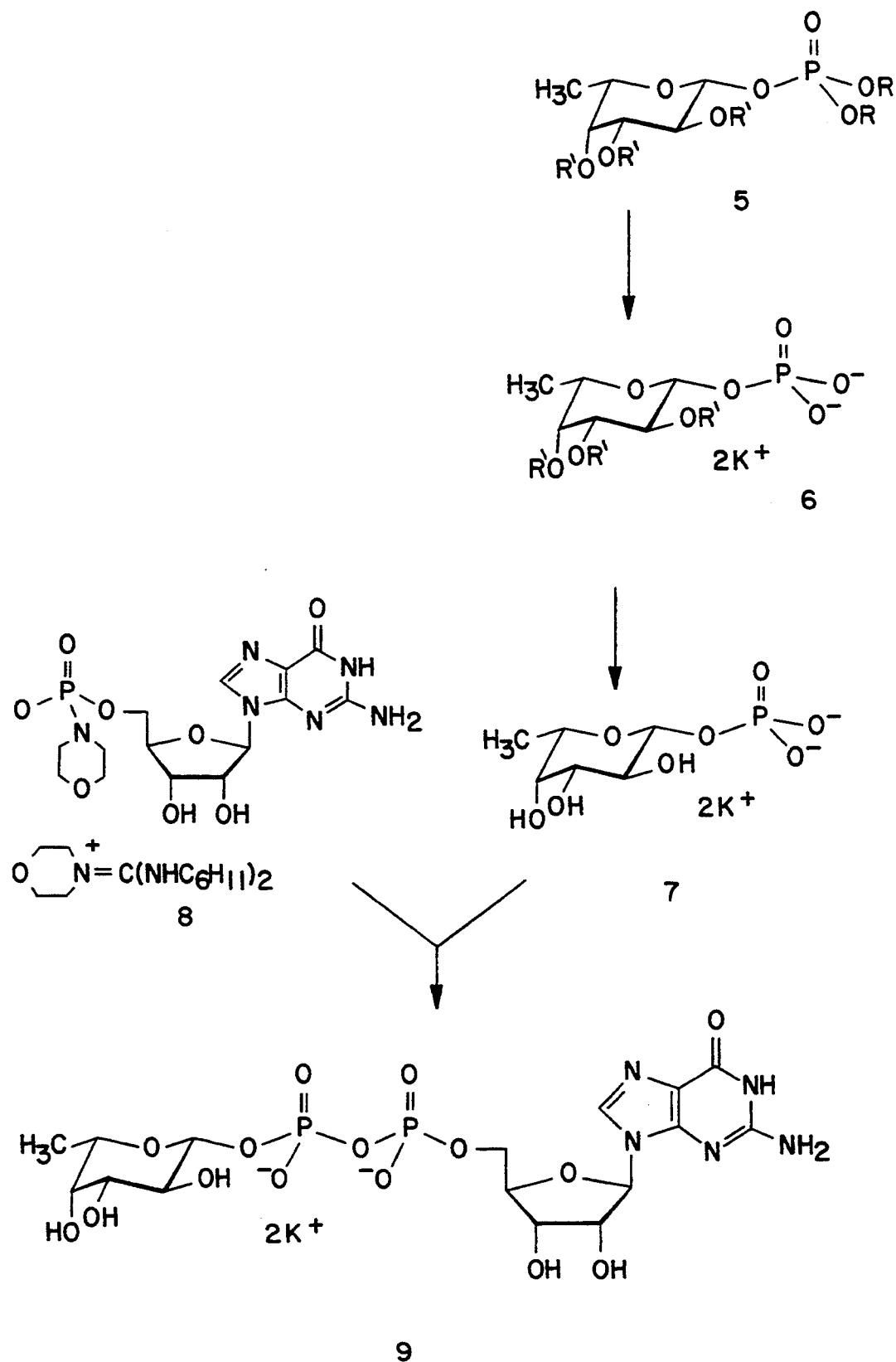
FIG. 2 is a synthesis scheme of the reaction of β-L-fucopyranosyl phosphate to give GDP-fucose. 5: 2,3,4-protected β-L-fucopyranosyl phosphate; 6: salt of 2,3,4-protected β-L-fucopyranosyl phosphate; 7: salt of unprotected β-L-fucopyranosyl phosphate; 8: salt of (activated) GMP morpholidate; 9: GDP-fucose (salt); the symbols here in each case mean: $R'=R^1CO-$, $R^1$; $R^1$=alkyl ($C_1-C_4$), benzyl, phenyl; $R=R^1$, K=preferably organic cation.

The figures in brackets after individual compounds in the following relate to the numbering in the figures.

Above and below, the radicals R, R' and $R^1$ have the meanings explained in greater detail below, if not expressly stated otherwise.

R and $R^1$ are $C_1-C_4$-alkyl, benzyl or phenyl. If R/$R^1$ is alkyl, these are in particular methyl, ethyl, n-propyl, isopropyl, n-butyl, isobutyl or sec- and tert-butyl; alkyl is in particular methyl.

R or $R^1$, however, is preferably benzyl. R' is $R^1CO-$ and $R^1$. For the synthesis of GDP-fucose starting from the β-L-fucopyranosyl phosphates, R' is preferably $R^1CO-$. In the radical $R^1CO-$, $R^1$ is preferably $CH_3-$ or $C_6H_4-$. $R^1$ is thus preferably acetyl or benzyl, but in particular acetyl. If $R^1$ is phenyl or benzyl, the aromatic rings can be mono- or polysubstituted. Suitable substituents are F, Cl, Br, OH or methyl. The aromatic rings, however, are preferably unsubstituted. $K^+$ is an inorganic or organic cation, preferably an organic cation of the formula $NH(R)_3^+$, in which $R^3$ is a straight-chain or branched, but preferably straight-chain alkyl having 1 to 10 C atoms. The cationic radicals $NH(C_2H_5)_3^+$ and in particular $NH(C_8H_{17})_3^+$ are preferred.

The meanings of a certain radical in a molecule can be identical or different; however, they are preferably identical.

The individual steps which relate to the modification of the hydroxyl groups of the fucose such as, for example, esterification, etherification, halogenation, transesterification, transetherification, hydrolysis, ether cleavage, protective group introduction and removal and glycosyl imidate formation correspond, if not otherwise described, to the common standard methods of carbohydrate chemistry. A comprehensive presentation of this standard technology is to be found, for example, in: Carbohydrate Chemistry (Editor John F. Kennedy), Oxford Science Publication, Clarendon Press, 1988.

The process according to the invention is preferably carried out as follows.

In order to carry out specific changes to the glycosidic C atom or to the anomeric carbon, as is known, the introduction of protective groups is required. Depending on the reactivity desired, ester or ether groups are preferred for this purpose. The process according to the invention in this connection prefers acetyl or benzyl as protective groups. However, the alternatives specified above in greater detail can also be employed successfully.

Synthesis of trisubstituted L-fucose (1):

2,3,4-Tri-O-benzyl-L-fucopyranose (1) can be prepared from L-fucose, for example, by the process of Wegmann et al. (Carbohydr. Res. 184 (1988), 254) or of Dejter-Juszynski et al. (Carbohydr. Res. 18 (1971), 219). According to the invention, however, the triacetylated L-fucose is preferably synthesized, as this is better suited for the further synthesis steps.

For the synthesis of 2,3,4-tri-O-acetyl-L-fucopyranose (1), according to the invention 1,2,3,4-tetra-O-acetyl-α-L-fucopyranose is reacted in a one-step reaction with, preferably, hydrazine acetate in dimethylformamide. For the specific hydrolysis of the anomeric acetyl group, benzylamine, potassium hydroxide, potassium cyanide or bis(tributyltin) oxide are also suitable in addition to hydrazine acetate.

The triacetylated product formed occurs in an α:β anomer ratio of on average 3:1. For further reaction and the stereoselectivity of the total process, this state of affairs, however, is insignificant. After purification via, for example, silica gel chromatography, the anomer mixture of the triacetylated L-fucopyranose is obtained in a yield of 75 to 85%. The corresponding product is prepared in the process of the prior art (Nunez et al., supra.) on the other hand in a complicated multi-step reaction and also not further purified. The starting material, 1,2,3,4-tetra-O-acetyl-α-L-fucopyranose, is, if it is not commercially available, easily accessible by the known process according to Nunez et al. or Prihar et al. (Biochemistry 12 (1973), 997).

Synthesis of the α- and β-trichloroacetimidates of trisubstituted L-fucopyranose (2,3):

2,3,4-Tri-O-acetyl-L-fucopyranose (1) or the correspondingly tribenzylated derivative (1) are now reacted with trichloroacetonitrile according to the known glycosyl imidate method (for example, Schmidt et al., Angew. Chem. 92 (1980), 763). The anomer ratio can be controlled depending on the type of base used. Surprisingly, when using sodium hydride, the O-(2,3,4-tri-O-acetyl/benzyl-α-L-fucopyranosyl)trichloroacetimidate(3) necessary for further synthesis is obtained exclusively, i.e., exclusively the α-anomer. The same result is obtained when using potassium hydride or sodium hydroxide. If, on the other hand, other bases such as DBU (1,2-diazabicyclo[5.4.0]undec-7-ene) or potassium carbonate are employed, an anomer mixture of α- and β-trichloroacetimidates having a ratio of about 7:1 to 1:1 is obtained. The process according to the invention therefore works preferably with bases which react like sodium hydride. Other such bases are routinely selectable by analogy to the known properties of sodium hydride. The α-trichloroacetimidate is preferably purified by chromatography and is then obtained in pure form with a yield of on average 70 to 80%.

Synthesis of trisubstituted L-fucopyranosyl phosphates (4,5)

By reaction of the trisubstituted α-trichloroacetimidates of L-fucose, prepared as described above, with organic phosphates of the formula PO(OH) (OR)$_2$, in which R is R$^1$ and R$^1$ has the above-mentioned meaning, the corresponding trisubstituted L-fucopyranosyl phosphates, preferably the dibenzyl 2,3,4-tri-O-acetyl/benzyl-α-L-fucopyranosyl phosphates (4) and the dibenzyl 2,3,4-tri-O-acetyl/benzyl-β-L-fucopyranosyl phosphates (5), are obtained in good yields. A suitable organic phosphate is thus preferably dibenzyl phosphate, on the one hand because it is easily obtainable and on the other because the benzyl group can be selectively removed particularly easily.

Of course, the other above-mentioned phosphates, such as, for example, diphenyl phosphate, are also suitable. However, the presence or the absence of acid during the course of the reaction is crucial to suitability for the stereoselective preparation of the phosphates having the α- or β-configuration. The pure α-anomers (4) are obtained when catalytic amounts of acids, such as, for example, boron trifluoride, are added to the mixture. If the phosphate employed is not too pure, even the addition of acid can be dispensed with. If, on the other hand, the reaction is carried out under absolutely acid-free conditions, the pure β-anomer (5) is obtained selectively. For this, it is as a rule necessary to freshly recrystallize the phosphate employed at least once or to take other appropriate measures which do not allow any acid catalysis.

The process for preparing (4) and (5) are conducted at a temperature of about 0°-30° C., preferably 15°-20° C., for 1-8 hours (nitrogen-atmosphere) and the proportions of the reactants are equimolar (imidate/phosphate).

The yields after purification are preferably between 85 and 90%, relative to the α-trichloroacetimidate of the protective L-fucose employed. Yields between 90 and 98% can be expected without special purification. The yields are not crucially dependent on the nature of the chosen ester protective group on the fucose ring. Purification can be successfully carried out, for example, by means of chromatography on, for example, silica gel.

Synthesis of β-L-fucopyranosylguanosine 5'-pyrophosphate (GDP-fucose) (9).

The β-fucopyranosyl phosphates protected on the fucose ring with ester groups, in particular the corresponding acetyl or benzoyl derivatives, are particularly suitable for further synthesis. In the following removal of the phosphate protective groups, preferably by hydrogenolysis, these protective groups are retained. The preferred substrate for further synthesis is accordingly dibenzyl or diphenyl 2,3,4-tri-O-acetyl-β-L-fucopyranosyl phosphate (5). Removal, preferably of the dibenzyl or diphenyl radical, can be carried out by standard methods, for example with palladium and hydrogen. However, other catalysts are also suitable for this without the fucose protective groups being hydrolyzed, for example platinum and nickel catalysts. Hydrolysis can also be effected with ammonium formate.

The resulting 2,3,4-tri-O-acetyl-β-L-fucopyranosyl phosphate (6) is preferably isolated as the salt, preferably as the bis-triethylammonium salt, and optionally purified by chromatography in a manner known per se. However, isolation can also be carried out as another salt, for example as the barium or bis-tri-n-butyl-ammonium salt. The course of the reaction can expediently be monitored by means of thin layer chromatography. The three protective groups, preferably acetyl, of the fucopyranosyl ring are then removed in a further step by standard methods in a manner known per se and the corresponding salt of the free β-L-fucopyranosyl phosphate (7) is obtained. This last step as a rule proceeds quantitatively. In a preferred embodiment of the process according to the invention, the β-fucopyranosyl phosphate thus obtained is then converted into the corresponding tri-n-octylammonium salt. This surprisingly proves to be particularly favorable in the subsequent last synthesis step, probably owing to its favorable solubility properties. Other comparable ammonium salts of the formula NH(R$^3$)$_3$+X−, in which R$^3$ has the meanings defined above, in particular in which R$^3$ is higher chain alkyl, are also especially suitable in this sense. The reaction of the bis-tri-n-octylammonium β-L-fucopyranosyl phosphate preferably used, to give the final product, GDP-fucose, of the synthesis according to the invention is carried out using guanosine monophosphate. It is indispensable here, as described in the literature, that GMP is employed in an activated form in order to achieve good reaction rates. Condensation with GMP-5'-phosphormorpholidate has proved particularly suitable. However, GMP activated in another known manner, as described, for example, in Nunez et al., can also be employed. In a preferred embodiment of the process, 4-morpholino-N,N'-dicyclohexylcarboxamidiniumguanosine 5'-monophosphoromorpholidate (8) is employed. The bis-tri-n-octylammonium salt of L-GDP-fucose (9) is formed with an average yield of about 70%. For further purification, the compound is again converted into the bis-triethylammonium salt which is more suitable for these purposes. According to the invention, a purification by means of HPLC is then carried out, preferably on reverse phase materials. It is furthermore crucial for good final yields of highly pure GDP-fucose and in accordance with a simple process technique that the synthesis of the final product is eluted with a volatile buffer system of a preferably preparative acid. A suitable eluant of this type which may be employed is in particular triethylammonium hydrogencarbonate. Those also suitable are alternatively ammonium hydrogencarbonate or ammonium formate.

The process for preparing GDP-fucose (9) is conducted under conditions similar to Nunez et al., supra.

The manner of purification described has the advantage that very pure GDP-fucose can be obtained very simply. Desalting, which according to the experience is always accompanied by losses in yield, can thus be dispensed with.

The following chromatography systems were generally used in these examples:

Thin layer chromatography: TLC plastic films silica gel 60 $F_{254}$ (E. Merck, Darmstadt, FRG), detection in UV light at 254 nm, or by means of spraying with 10% $H_2SO_4$ and heating to 110° C.

Column chromatography: Silica gel 60, particle size 0.063–0.200 nm (E. Merck, Darmstadt, FRG).

Analytical HPLC: LiChrospher RP-18, 125×4 mm, 5 μm (E. Merck, Darmstadt, FRG), buffer: 0.05M triethylammonium hydrogencarbonate (pH 7.1) 3.5% of acetonitrile, 0.5 ml/min. $R_f$=3.24 min (GMP), 3.85 min (GDP-fucose), 12.7 min (GMP-morpholidate).

Preparative HPLC: LiChrosorb RP-18, 250×10 mm, 7 μm (E. Merck, Darmstadt, FRG) buffer as above.

The intermediates/final products synthesized were identified by means of $^1$H-NMR and $^{13}$C-NMR and their degree of purity was determined.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 41 02 817.1, filed Jan. 31, 1991, are hereby incorporated by reference.

EXAMPLES

EXAMPLE 1

A solution of 2,3,4-tri-O-benzyl-L-fucopyranose (prepared, for example, according to Wegmann et al., supra.) (0.50 g, 0.86 mmol) in 20 ml of dry dichloromethane and commercially available dibenzyl phosphate which is not further purified (0.24 g, 0.86 mmol) is stirred under a nitrogen atmosphere at room temperature for about 2 h. In the case of very pure dibenzyl phosphate, a catalytic amount of boron trifluoride is added to the mixture. The solution is then concentrated and purified by chromatography (toluene/acetone 9:1). Dibenzyl 2,3,4-tri-O-benzyl-α-L-fucopyranosyl phosphate (4) is obtained in a yield of 90% as a colorless oil (0.54 g). TLC (toluene/acetone 7:1) gives an $R_f$ of 0.60, $[\alpha]_{578}$=−68.2 (c=1, chloroform).

EXAMPLE 2

A solution of 2,3,4-tri-O-benzyl-L-fucopyranose (0.50 g, 0.86 mmol) in 20 ml of dry dichloromethane and freshly recrystallized dibenzyl phosphate (0.24 g, 0.86 mmol) is stirred under a nitrogen atmosphere at room temperature for about 1 h. The solution is then concentrated and purified by chromatography (toluene/acetone 7:1). Dibenzyl 2,3,4-tri-O-benzyl-β-L-fucopyranosyl phosphate (5) is obtained in a yield of 95% as a colorless oil (0.57 g). TLC (toluene/acetone 7:1) gives an $R_f$ of 0.45, $[\alpha]_{578}$=−9.7 (c=1, chloroform).

EXAMPLE 3

A solution of 1,2,3,4-tetra-O-acetyl-α-L-fucopyranose (6.00 g, 18 mmol), prepared, for example, according to Nunez et al., supra., and hydrazine acetate (1.99 g, 21.6 mmol) in 20 ml of dry dimethylformamide is stirred at 50° C. for 4.5 h. After addition of ethyl acetate, the mixture is extracted about twice with aqueous sodium chloride solution and the concentrated organic extract is chromatographed (petroleum ether (40°–60°)/ethyl acetate 1:1). 2,3,4-Tri-O-acetyl-L-fucopyranose (1) is obtained in an anomer ratio of α:β of 3:1 with a yield of 80%. TLC analysis (petroleum ether (40°–60°)/ethyl acetate 1:1) gives $R_f$=0.47.

EXAMPLE 4

(a) Sodium hydride (0.25 g, 10.9 mmol) is added under nitrogen and at room temperature to a mixture of 2,3,4-tri-O-acetyl-L-fucopyranose (anomer mixture) (2.00 g, 6.89 mmol) and trichloroacetonitrile (7.0 ml, 70 mmol) in 20 ml of dry dichloromethane. The mixture is stirred for about 12 h and then filtered through kieselguhr and concentrated. After chromatographic purification (petroleum ether/ethyl acetate 3:1), O-(2,3,4-tri-O-acetyl-α-L-fucopyranosyl) trichloroacetimidate (3) is obtained in a yield of 71% (2.13 g).

(b) A mixture of 2,3,4-tri-O-acetyl-L-fucopyranose (anomer mixture) (0.50 g, 1.72 mmol), lithium chloride (73 mg, 1.72 mmol), 1,8-diazabicyclo-[5.4.0]-undec-7-ene (0.20 ml, 1.34 mmol) and trichloroacetonitrile (2.0 ml, 20 mmol) in 20 ml of dry acetonitrile is stirred under nitrogen and at room temperature for about 12 h. After chromatographic purification (petroleum ether/diethyl ether 2:5), a mixture of O-(2,3,4-tri-O-acetyl-α-L-fucopyranosyl) trichloroacetimidate (3) and O-(2,3,4-tri-O-acetyl-β-L-fucopyranosyl) trichloroacetimidate (2) is obtained in a yield of 92% (α:β=6.5:1).

c) A mixture of 2,3,4-tri-O-acetyl-L-fucopyranose (anomer mixture) (0.85 g, 2.93 mmol), trichloroacetonitrile (3 ml, 30 mmol) and potassium carbonate (2.73 g, 19.7 mmol) in dry dichloromethane (12 ml) is stirred under nitrogen at room temperature for about 4 h. After filtration through kieselguhr, the solvent is removed. After chromatographic purification (petroleum ether/diethyl ether 2:5), a mixture of O-(2,3,4-tri-O-acetyl-α-L-fucopyranosyl) trichloroacetimidate (3) and O-(2,3,4-tri-O-acetyl-β-L- fucopyranosyl) trichloroacetimidate (2) is obtained in a yield of 76% ($\alpha$:$\beta$=1:1.3). $\alpha$-Anomer: $[\alpha]_D$=−116.0 (c=1, chloroform), $R_f$=0.54 (petroleum ether/ethyl acetate 2:1), m.p. 107°–109° C. $\beta$-Anomer: $[\alpha]_D$=−24.5 (c=1, chloroform), $R_f$=0.34 (petroleum ether/ethyl acetate 2:1), m.p. 60°–63° C.

EXAMPLE 5

A solution of O-(2,3,4-tri-O-acetyl-$\alpha$-L-fucopyranosyl) trichloroacetimidate (0.20 g, 0.46 mmol) in dry dichloromethane (7 ml) and commercially available dibenzyl phosphate which is not purified further (0.13 g, 0.47 mmol) is stirred under nitrogen at room temperature for about 2.5 h. In the case of very pure dibenzyl phosphate, a catalytic amount of boron trifluoride is added to the mixture. The solution is then concentrated and purified by chromatography (toluene/acetone 7:1) and rechromatographed (chloroform/diethyl ether 20:1). Dibenzyl 2,3,4-tri-O-acetyl-$\alpha$-L-fucopyranosyl phosphate (4) is obtained in a yield of 91% as a colorless oil (0.23 g). TLC (toluene/acetone/triethylamine 84:15:1) gives an $R_f$ of 0.38, $[\alpha]_D$=−83.7 (c=1, chloroform).

EXAMPLE 6

A solution of O-(2,3,4-tri-O-acetyl-$\alpha$-L-fucopyranosyl) trichloroacetimidate (0.50 g, 1.15 mmol) in dry dichloromethane (25 ml) and commercially available diphenyl phosphate which is not purified further (0.29 g, 1.16 mmol) is stirred under nitrogen at room temperature for about 6.5 h. In the case of very pure dibenzyl phosphate, a catalytic amount of boron trifluoride is added to the mixture. The solution is then concentrated and purified by chromatography (petroleum ether/diethyl ether 1:5). Diphenyl 2,3,4-tri-O-acetyl-$\alpha$-L-fucopyranosyl phosphate (4) is obtained in a yield of 63% as a colorless oil (0.38 g). TLC (petroleum ether/diethyl ether 1:5) gives an $R_f$ of 0.41.

EXAMPLE 7

A solution of O-(2,3,4-tri-O-acetyl-$\alpha$-L-fucopyranosyl) trichloroacetimidate (0.30 g, 0.69 mmol) in dry dichloromethane (12 ml) and commercially available, but freshly recrystallized, dibenzyl phosphate (0.19 g, 0.68 mmol) is stirred under nitrogen at room temperature for about 1 h. The solution is then concentrated and chromatographed: (toluene/acetone 7:1) and rechromatographed (petroleum ether/diethyl ether 1:5). Dibenzyl 2,3,4-tri-O-acetyl-$\beta$-L-fucopyranosyl phosphate (5) is obtained in a yield of 86% as a colorless oil (0.36 g). TLC (toluene/acetone 7:1) gives $R_f$ of 0.30, $[\alpha]_D$=+0.5 (c=1, chloroform).

EXAMPLE 8

A mixture of dibenzyl 2,3,4-tri-O-acetyl-$\beta$-L-fucopyranosyl phosphate (5) (72 mg, 0.13 mmol) and palladium (4 mg) in 10 ml of dry tetrahydrofuran/ethyl acetate (1:1) is shaken under $H_2$ atmosphere. The end of the reaction is determined by means of TLC ($R_f$=0.19, chloroform/methanol 60:40). The mixture is filtered, concentrated and chromatographed (chloroform/methanol/triethylamine 60:39:1). After lyophilization in dioxane, bis-triethylammonium 2,3,4-tri-O-acetyl-$\beta$-L-fucopyranosyl phosphate (6) is obtained in a yield of 90% (68 mg) as an amorphous powder.

EXAMPLE 9

0.5 ml of triethylamine is added to a solution of bis-triethylammonium 2,3,4-tri-O-acetyl-$\beta$-L-fucopyranosyl phosphate (80.0 mg, 0.135 mmol) in 3 ml of methanol/water mixture. After 18 h, the mixture is concentrated and lyophilized from water. Bis-triethylammonium $\beta$-L-fucopyranosyl phosphate (7) is obtained in a yield of 100% (73.8 mg) as a hygroscopic white powder which is not further purified.

EXAMPLE 10

Tri-n-octylamine (0.117 ml, 0.135 mmol) is added to a solution of bis-triethylammonium $\beta$-L-fucopyranosyl phosphate (73.8 mg, 0.135 mmol) in dry pyridine (5 ml). The mixture is concentrated and the resulting tri-n-octylammonium salt is dried by repeated evaporation with pyridine at $10^{-2}$ torr. After addition of 4-morpholino-N,N'-dicyclohexylcarboxamidinium guanosine 5'-monophosphoromorpholidate (8) (109 mg, 0.15 mmol) in dry pyridine/dimethylformamide (1:1), the reaction is monitored by means of analytical HPLC. After about 5 days, the mixture is concentrated to dryness. The residue is taken up in triethylammonium hydrogencarbonate buffer (pH 7.4, 0.05M), tri-n-octylamine is removed by extraction with ether, and the mixture is finally purified by means of preparative HPLC ($t_R$=9.4 min) and the buffer used as the eluant is evaporated. Very pure bis-triethyl-ammonium ($\beta$-L-fucopyranosyl)guanosine 5'-pyrophosphate (9) is obtained in a yield of 25% (23.3 mg) as an amorphous powder.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the stereoselective preparation of a $\beta$-L-fucopyranosyl phosphate comprising:
   a) reacting L-fucose protected in positions 2, 3 and 4 with trichloroacetonitrile to form O-($\alpha$-L-fucopyranosyl) trichloroacetimidate;
   b) reacting the O-($\alpha$-L-fucopyranosyl)trichloroacetimidate with an acid-free organic phosphate of the formula PO(OH)(OR)$_2$, wherein R is $C_1$–$C_4$-alkyl, phenyl or benzyl;
   c) removing the radical R of the phosphate group by hydrogenolysis and the protective groups by an alcohol on the fucopyranosyl ring; and
   d) recovering the $\beta$-L-fucopyranosyl phosphate salt.

2. A process according to claim 1, wherein the protective groups on the fucopyranosyl ring is acetyl or benzyl.

3. A process according to claim 1, wherein the organic phosphate is diphenyl or dibenzyl phosphate.

4. A process according to claim 1, wherein the organic phosphate is freshly recrystallized prior to the reaction with protected L-fucose.

5. A process according to claim 1, wherein the protected L-fucose is reacted selectively with sodium hydride, sodium hydroxide, or potassium hydride to obtain the O-($\alpha$-fucopyranosyl) trichloro-acetimidate.

6. A process according to claim 1, wherein protected L-fucose is 2,3,4-tri-O-alkyl-L-fucose, 2,3,4-tri-O-phenyl-L-fucose or 2,3,4-tri-O-benzyl-L-fucose.

7. A process according to claim 6 further comprising preparing 2,3,4-tri-O-acetyl-L-fucose by hydrolyzing tetra-O-acetylated L-fucose in a one-step reaction.

8. A process according to claim 7, wherein the anomeric acetyl group of the tri-O-acetyl-L-fucose is removed with hydrazine acetate.

9. A process for the stereoselective preparation of guanosine diphosphate-fucose (GDP-fucose), comprising:

reacting an easily soluble salt of $\beta$-L-fucopyranosyl phosphate, obtained by a process according to claim 1, with an activated guanosine monophosphate (GMP) morpholidate.

10. A process according to claim 9, wherein the $\beta$-L-fucopyranosyl phosphate salt is the tri-n-octylammonium salt.

11. A process according to claim 9, further comprising recovering the GDP-fucose.

12. A process according to claim 9, further comprising purifying the GDP-fucose by means of preparative HPLC using a volatile buffer eluant system.

13. A process for the preparation of $\beta$-fucopyranosyl phosphates comprising reacting O-($\alpha$-L-fucopyranosyl)trichloroacetimidate of protected L-fucose with an acid-free organic phosphate of the formula $PO(OH)(OR)_2$ wherein R is $C_1$–$C_4$ alkyl, phenyl or benzyl.

14. A process for the preparation of $\beta$-fucopyranosyl phosphate according to claim 13, wherein the reaction is conducted at a temperature of 0°–30° C. for 1–8 hours and the proportion of the reactants are equimolar.

15. A process for the preparation of $\beta$-fucopyranosyl phosphate according to claim 14, wherein the temperature is 15°–20° C.

16. A process for the preparation of guanosine diphosphate (GDP) fucose comprising reacting the tri-n-octylammonium salt of $\beta$-L-fucopyranosyl phosphate with activated guanosine monophosphate (GMP), to form GDP fucose.

17. A process for the preparation of 2,3,4-tri-O-acetyl L-fucose comprising removing the anomeric acetyl group of tetra-O-acetylated L-fucose with hydrazine acetate.

* * * * *